United States Patent [19]

Mertens

[11] Patent Number: 5,780,008

[45] Date of Patent: Jul. 14, 1998

[54] POLYHDRIC PHENOL COMPOUNDS

[75] Inventor: John Janine Rene Mertens, Vilvoorde, Belgium

[73] Assignee: Mallinckrodt Medical, Inc., St. Louis, Mo.

[21] Appl. No.: 842,698

[22] Filed: Apr. 15, 1997

Related U.S. Application Data

[63] Continuation of Ser. No. 491,841, filed as PCT/US93/12272, Dec. 16, 1993.

[51] Int. Cl.⁶ .......................... A61K 51/00; A61M 36/14
[52] U.S. Cl. .......................... 424/1.73; 424/1.85; 424/1.11; 549/200; 549/356
[58] Field of Search .......................... 424/1.11, 1.37, 424/1.65, 1.73, 1.81, 1.85, 9.1, 9.3, 9.4, 9.5, 9.6; 549/200, 356, 358; 540/1

[56] References Cited

FOREIGN PATENT DOCUMENTS 9414477   7/1994   WIPO .

OTHER PUBLICATIONS

Bandyukova et al. (1987), Rastit. Resur., 23(4), Abstract, "Anti–bacterial Activity of Flavonoids of Some Flowering Plant Species".
Mertens et al (1994), J. Labelled Compounds and Radiopharmaceuticals, 34 (11), pp. 1011–1021, The Radiosynthesis of a New Potential Glucose Transport Protein Tracer: 3-[$^{125}$I] Iodophloretin.

*Primary Examiner*—Jose G. Dees
*Assistant Examiner*—Dameron Jones

[57] ABSTRACT

The invention relates to polyhydric phenol compounds of the general formula

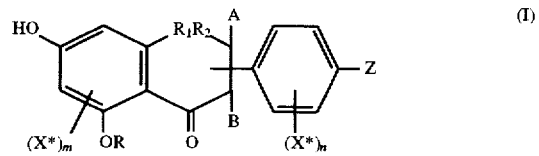

wherein R is a hydrogen atom or a saccharide moiety;

A and B are hydrogen atoms or form together a C—C bond;

$R_1$ is a hydroxy group and $R_2$ is a hydrogen atom, or $R_1$ and $R_2$ form together an oxygen atom;

Z is a hydroxy group, an amino group, a carboxy group or a N-(carboxymethyl)carbamoyl group;

X* is a radioactive halogen isotope; and m and n are 0 or 1, with the proviso, that m is 1 if n is 0, and that m is 0 if n is 1.

The radiolabelled phenol compounds can be used for diagnosis and therapy.

9 Claims, 3 Drawing Sheets

POLYHDRIC PHENOL COMPOUNDS

This is a contiuation of application Ser. No. 08/491,841, filed as PCT/US93/12272, Dec. 16, 1993.

The present invention relates to polyhydric phenol compounds, to a method of preparing these compounds, to a pharmaceutical composition comprising these compounds and to the use of this composition for diagnosis and therapy.

It is shown in literature, e.g. by LeFevre et al. (J. Biol.Chem., 1959, 234, 3022–3026), that phloretin is an inhibitor of glucose transport processes. It is also known from literature (e.g Ogawara et al., J. Antibiotics, 1986, 39, 606–608; Akiyama et al., J. Biol. Chem., 1987, 262, 5592–5593; and Linassier et al.,m Biochem. Pharmacol., 1990, 39, 187–193), that genistein inhibits the tyrosine kinase activity.

It is well-known in the art (see e.g. Berry et al., J. Nucl. Med., 1991, 32, 1518–1525), that fluorodeoxyglucose (FDG) accurately traces glucose transport. In this connection $^{18}$F-FDG has been developed as an imaging agent for detecting and locating various diseases and disorders where glucose transport plays a part. Although $^{18}$F-FDG is generally considered as a useful PET imaging agent, the PET technique is usually not the technique of choice for diagnosing purposes. As correctly stated by Lutz et al. (J. Label. Comp. Radiopharm., 1991, 29, 535–545), "there is no question that more patients would benefit if a glucose analogue could be labelled with a single photon emitting radionuclide such as $^{123}$ I". . Such a radioactive-iodine labelled glucose analogue would allow the use of simple gamma detection devices and, if desired, the application of the more advanced SPECT technique.

Lutz et al. indeed have succeeded in labelling glucose analogues with $^{123}$ r, viz. by synthetizing the various isomers of 123-iodobenzyl-deoxyglucose. The test results obtained by these authors, however, were disappointing, because biodistribution studies showed, that the overall tissue uptake was too low for these glucose analogues to offer perspectives for use as imaging agents. Apparently, the introduction of radioactive iodine in the deoxyglucose molecule has an adverse influence on the in vivo stability of this compound, so that transport of radioactivity into the relevant tissues is virtually prevented.

It is the main objective of the present invention to provide a diagnostic agent for pathologies, related to a disturbed—generally increased—glucose metabolism, and/ or for tumour cells, which agent is labelled with a suitable isotope to allow its detection by gamma detection devices.

This objective can be achieved by new polyhydric phenol compounds which, according to the present invention, have the general formula (I)

wherein

R is a hydrogen atom or a saccharide moiety;

A and B are hydrogen atoms or form together a C—C bond;

$R_1$ is a hydroxy group and $R_2$ is a hydrogen atom, or $R_1$ and $R_2$ form together an oxygen atom;

Z is a hydroxy group, an amino group, a carboxy group or a N-(carboxymethyl)carbamoyl group;

X* is a radioactive halogen isotope; and m and n are 0 or 1, with the proviso, that m is 1 if n is 0, and that m is 0 if n is 1.

Surprisingly it has been found, that the radiohalogenated polyhydric phenol compounds of the present invention, in particular labelled with radioisotopes of Br and I, are easily transported by plasma proteins to the relevant tissues, and consequently show an identical behaviour to the acceptor sites in the tissues as the corresponding unlabelled compounds, for example, unlabelled phioretin, the properties of which are described by LeFevre et al. (see above).

Examples of radiohalogenated polyhydric phenol compounds of the invention are:

(1) radiohalogenated phloretin, (2) radiohalogenated genistein, and (3) radiohalogenated naringenin,

(4) as well as their carbohydrates, such as radiohalogenated phlorizin, as well as their analogues, wherein the 4-hydroxy group (Z) is replaced by:

(5) an amino group, (6) a carboxy group, (7) a (N-carboxymethyl)carbamoyl group.

In connection with the chemical stability and the synthetic accessibility, compounds are preferred which have the general formula (II)

wherein

R, $R_1$, $R_2$, Z, A and B have the meanings given above; and

Y* is a radioactive halogen isotope selected from $^{123}$I, $^{124}$I, $^{125}$I, $^{131}$I, $^{75}$Br, $^{76}$Br, $^{77}$Br and $^{82}$Br.

As will be described hereinafter, compounds of the above general formula II, wherein Y* is selected from $^{124}$I, $^{125}$I and $^{131}$I, are in particular useful for tumour therapy.

Pre-eminently suitable compounds of the invention are radiolabelled phloretin and its carbohydrates, which can be represented by the general formula (III)

wherein

R, Z and Y* have the meanings given above.

The new radiohalogenated polyhydric phenol compounds of the invention can be prepared in a manner known per se for related compounds. So the invention also relates to a method of preparing a radiohalogenated polyhydric phenol compound, as defined hereinbefore, of high specific radioactivity, characterized in that a compound of the general formula (IV)

wherein

R, R₁, R₂, Z, A, B, Y*, m and n have the meanings given above; is prepared by reacting a compound of the general formula (V)

wherein

Y is a non-radioactive, bromine atom or iodine atom; with a water-soluble halogenide, selected from $^{123}$I, $^{124}$I, $^{125}$I, $^{131}$I, $^{75}$Br, $^{76}$Br, $^{77}$Br and $^{82}$Br, in the presence of copper(I) ions, a water-soluble acid and a reducing agent.

Such a halogen exchange reaction is described in European Patent No. 165630. An example of a suitable water-soluble acid is ascorbic acid; examples of suitable reducing agents are Sn(II) salts, ascorbic acid, gentisic acid, isoascorbic acid, a monosaccharide and a sulphite.

Various polyhydric phenols, such as phloretin, genistein, naringenin, phlorizin, and the like, are available for producing the starting compounds for the above halogen exchange reaction. These polyhydric phenols contain two benzene rings, one of which is provided with three (hydr)oxy substituents. This latter benzene ring is therefore more activated and is preferentially substituted in an electrophilic substitution, e.g. an iodination, radioiodination, bromination or radiobromination reaction. It has been observed, however, that the polyhydric phenol compound, after iodination or bromination in the tri(hydr)oxyphenyl moiety, is not always sufficiently stable under the conditions applied, so that such starting compounds for the above halogen exchange reaction are preferred, wherein the halogen substituent is attached to the mono-hydroxyphenyl moiety. The 4-NH₂ analogues (Z=NH₂), showing the same behaviour, are well accessible by a coupling reaction of phloroglucinol (or a hydroxy-protected derivative thereof) with a suitable nitrile, e.g. 4-aminophenyl-proprionitrile, in a corresponding manner as described in U.S. Pat. No. 2,789,995.

As a special feature of the present invention it has been found, that the instable character of the polyhydric phenol compound, brominated in the tri(hydr)oxyphenyl moiety, can be used in favour of the synhesis of such preferred starting compounds. Therefore, the invention also relates to a method of preparing a compound to be used as a starting compound for the above-defined-halogen exchange reaction, characterized in that a halo-substituted polyhydric phenol compound of the general formula

(VI)

wherein Z' is a hydroxy group or an aminogroup, and the other symbols have the meanings given above; is prepared by:

(a) brominating a compound of the general formula (VII)

in the presence of a water-soluble acid, producing a compound of the general formula (VIII)

followed by (b) a debromination reaction under the influence of a suitable reducing agent and a strong water-soluble base, producing a compound of the general formula VI, wherein Y is a bromo substituent; and, if desired, followed by

(c) a halogen exchange reaction as described above in order to substitute a iodo substituent for the bromo substituent in said compound of formula VI.

As will become apparent from the accompanying Examples, the successive brominating and debrominating reactions proceed smoothly, producing the desired monobromo-substituted product in a high yield and purity. Examples of suitable reducing agents are sulfite and thiosulfate.

Other suitable starting compounds for the above-defined halogen exchange reaction can be represented by the formulas

(IX)

and (XI)

The compound of formula IX can be prepared in a manner known per se for related compounds from a compound of the general formula (X)

obtained a described above.

Preferably the formula X compound is converted to its diazonium salt, which compound is then carboxylated to substitute a —COOH group for the —N$_2$$^+$ substituent. The carboxylation reaction can conveniently be carried out with carbon monoxide and sodium acetate in the presence of a noble-metal catalyst such as palladium acetate.

The compound of formula XI can be prepared in a manner known per for related compounds. from a hydroxy-protected derivative of compound IX, viz. from a compound of the general formula (XII)

wherein P is a hydroxy-protecting group,

R$_1$' is a protected hydroxy group or forms together with R$_2$ an oxygen atom, and which compound can be obtained in a corresponding manner as said formula IX compound.

Preferably the carboxy group of the formula XII compound is first derivatized to allow reaction with glycine. A suitable derivatizing agent is N-hydroxysuccinimide to produce the N-succinimidyl ester of the formula XII compound, which smoothly reacts with glycine to produce, after deprotection of the phenolic hydroxy groups, the desired compound of formula XI.

The phenolic hydroxy groups may be protected in the form of alkyl ethers. e.g. methyl ethers, or as silyl ethers, e.g. trialkylsilyl ethers. Deprotection depends on the type of the protecting group: deprotection of alkyl ethers may occur e.g. with a borium trihalogenide, deprotection of silyl ethers e.g. with a fluoride, e.g. a tetraalkylammonium fluoride.

Certain substituted 4H-1-benzopyran-4-ones are also suitable starting compounds for the above halogen exchange reaction. These compounds, having the general formula (XIII)

wherein Y and Z' have the above-defined meanings, are prepared by converting a compound of the general formula (XIV)

wherein P is a hydroxy-protecting group, and which compound can be obtained in a corresponding manner as the above formula VI compound, with sodium and ethyl formate, followed by deprotection of the phenolic hydroxy groups.

The above-defined halo-substituted polyhydric phenol compounds of the general formulas VI, IX, XI and XII are new. Therefore the present invention also relates to these halo-substituted polyhydric phenol compounds per se, which can be presented by the general formula (XV)

wherein the symbols have the above meanings.

These compounds of formula XV may be used as intermediates in the synthesis of the radiolabelled compounds of the general formula I. In addition it has been found, that the new polyhydric phenol compounds of formula XV are potentially useful therapeutic agents.

The invention further relates to a pharmaceutical composition, comprising in addition to a pharmaceutically acceptable carrier material and, if desired, at least one pharmaceutically acceptable adjuvant, as the active substance a radiohalogenated polyhydric phenol compound as defined above.

The invention also relates to a method of detecting and locating tissues and/or processes, having a disturbed glucose metabolism and/or an increased tyrosine kinase activity, in the body of a warm-blooded living being, which comprises (i) administering to said being a composition comprising, in a quantity sufficient for external imaging, a radiolabelled polyhydric phenol compound as defined hereinbefore, wherein the radioactive halogen isotope is selected from $^{123}$I, $^{131}$I, $^{75}$Br, $^{76}$Br and $^{77}$Br, and thereupon (ii) subjecting said being to external imaging to determine the targeted sites in the body of said being in relation to the background activity.

The above-defined halogen isotopes are particularly suitable for diagnostic purposes. The such-labelled polyhydric phenol compounds are promising tools in the detection and location of tissues and/or processes, having a disturbed glucose metabolism and/or an increased tyrosine kinase activity, already in an early stage of their development, so that a therapeutic treatment can be chosen which is most effective for the patient in question.

The invention also relates to a method of intraoperatively detecting and locating tissues, having a disturbed glucose metabolism and/or an increased tyrosine kinase activity, in the body of a warm-blooded living being, which comprises (1) administering to said being a composition comprising, in a quantity sufficient for detection by a gamma detecting probe, a radiolabelled polyhydric phenol compound as defined hereinbefore, wherein the radioactive halogen isotope is $^{123}$I or $^{125}$I, preferably $^{125}$I, and thereupon (ii), after allowing the active substance to be taken up in said tissues and after blood clearance of radioactivity, subjecting said being to a radioimmunodetection technique in the relevant area of the body of said being, by using a gamma detecting probe.

The above iodine-isotope, viz. in particular $^{125}$I, allows the use of a such-labelled polyhydric phenol compound in the technique of radioguided surgery, wherein relevant tissues in the body of a patient can be detected and located intraoperatively by means of a gamma detecting probe. The surgeon can, intraoperatively, use this probe to find the lesions in which uptake of the compound labelled with $^{123}$I or $^{125}$I, preferably with $^{125}$I, which is a low-energy gamma photon emittor, has taken place.

It is known from literature, e.g. from a publication by Flier et al. in Science 1987, 235, 1492-1495, that most tumour cells display an increased glucose uptake. Therefore, the polyhydric phenol compounds of the invention, provided they are radiolabelled with isotopes suitable for this purpose, can be used for the therapeutic treatment of these tumours. So the invention finally relates to a method of therapeutically treating tumours, having an increased glucose uptake and/or an increased tyrosine kinase activity, in the body of a warm-blooded living being, which comprises administering to said being a composition comprising, in a quantity effective for combating or controlling tumours, a radiolabelled polyhydric phenol compound as defined hereinbefore, wherein the radioactive halogen isotope is selected from $^{124}$I, $^{125}$I and $^{131}$I.

The invention will now be described in greater detail with reference to the following specific Examples.

EXAMPLE I

Preparation of radiohaloQenated phloretin (a). Synthesis of 3-bromophloretin
Reaction equations:

Experimental Part:

To a solution of 41 mg phloretin (5) in 15 ml 100% HOAC are added 50 µl bromine, dissolved in 1 ml 100% HOAc. The bromination reaction is followed on HPLC (reverse phase RP18column, MeOH/acetate buffer 45/55, pH 4.8). After complete conversion to 3-bromo-3',5'-dibromophloretin (6), the reaction is stopped by addition of a saturated sodium sulphite solution. Then 20 ml MeOH is added and the obtained solution is evaporated to dryness.

The debromination is carried out by adding successively 5 ml bidistillated water and 1 ml saturated sodium sulphite solution to the residue. The obtained suspension is adjusted to pH 9 by 0.3 N NaOH solution and allowed to stand for 15 min. After adjusting the pH to 1.5 with diluted sulphuric acid, the solution is filtered and dried. The desired product (7) is obtained after successive recrystallization from MeOH/H$_2$O and extraction with diisopropylether in a yield of 49 mg. The product obtained is identified by HPLC (see above) and appeared to be 99% pure compound (7). The identity of this final product is confirmed by NMR and MS.

NMR: δ=6.8(Ha), 6.98(Hb) and 7.28(Hy); |calculated: 6.6, 6.95 and 7.2, respectively|.

MS: m/e=352-354 |calculated: 353|.

(b). Synthesis of 3-$^{131}$I-phloretin

The halogen exchange reaction is carried out by dissolving 1.2 mg 3-bromophloretin, obtained according to (a) above, into 5 µl 100% HOAc, and adding 450 µl stock solution and 60 µl Cu-solution to this solution of the phloretin compound.

stock solution:
2.5 mg tin sulphate
25 mg gentisic acid
35 mg citric acid
25 µl 100% HOAc
2.25 ml bidist. water.

Cu-solution:
32.5 mg CuSO$_4$.5H$_2$O
10 ml bidist. water.

The obtained solution is flushed with nitrogen for 5 min. After addition of 2.2 mCi $^{131}$I (as sodium iodide solution), the reaction mixture is kept at 140° C. for 60 min. The labelling yield is 65%. After filtration and dilution of the filtrate with MeOH/acetate buffer 45/55, pH 4.8, the obtained solution is purified by HPLC (see above). The separated 3-$^{131}$I-phloretin solution is collected, preconcentrated and eluted with 250 µl EtOH, yielding the desired product with an activity of 0.92 mCi.

In a corresponding manner 3-$^{125}$I-phloretin and 3-$^{123}$I-phloretin are prepared from 3-bromophloretin, using $^{125}$I-sodium iodide and $^{123}$I-sodium iodide, respectively.

EXAMPLE II

Preparation of radiohalogenated genistein (a) p-Methoxybenzylcyanide (0.50 g; 3.4 mmol) is dissolved in 5 ml diethylether. To this solution are added 0.29 g zinc chloride (2.1 mmol) and 0.49 g dimethoxyphloroglucine (3.2 mmol). A dry HCl gasflow is lead through the solution for 1. 5 hour. After evaporation of the solvent and dissolving the residue in 5 ml water, the reaction mixture is refluxed for 2 hours. After cooling of the solution, a mixture of isomers (8) and (9) is obtained in a yield of 65%.

The mixture is dissolved in diethylether and extracted with an aqueous alkaline solution to separate (8) from (9).

9

The desired isomer (8) remains in the organic phase and can be isolated by evaporation of the diethylether.

(b) The compound (8) obtained is brominated in a corresponding manner as described in Example I(a) to yield the desired 3-Br-substituted product (10) having the formula

(c) The product is converted to the 4H-1-benzopyran-4-one compound (11) by dissolving 0.442 g of compound (10) (11.6 mmol) in 35 ml ethyl formate. To this solution is added 2.39 g pulverized sodium portionwise. After stirring overnight under external cooling, some ice is added and the reaction mixture is acidified with hydrochloride acid. The product obtained (11) is distilled under diminished pressure and can be recrystallized from methanol.

(d) This product (11) is deprotected by dissolving 3.6 mmol in 5 ml dichloromethane and externally cooling in dry ice/isopropanol, after which 1.2 ml (12 mmol) borotribromide is added under an inert atmosphere. The solution is stirred for 30 minutes without external cooling and then stirred for another 30 minutes at 0° C. After saturation with NaCl the reaction mixture is extracted with dichloromethane. The organic phase is dried and concentrated. The desired demethylated product is obtained in a quantitative yield (e) The final product is obtained by a halogen exchange reaction with $^{123}$I, in a corresponding manner as described in Example I(b), using $^{123}$I as a sodium iodide solution. The desired product is obtained:

product (12)

EXAMPLE III

Preparation of radiohalogenated 4-amino-phloretin analogue

(a) To 4.95 g aniline (53.128 mmol) are added 2.82 g acrylonitrile (53.128 mmol) and 3.89 ml heptane. A dry HCl gasflow is lead through the solution. Aluminiumchloride (4.10 g; 30.726 mmol) is added portionwise in 2.5 hours. The HCl flow is stopped and the reaction mixture is stored overnight at 0° C. After reflux for 1 hour, the reaction mixture is poured on ice, and dichloromethane is added. The organic phase is washed with 10% aqueous KCl-solution (4x) and, after drying, evaporated. The oil obtained is purified by column chromatography, yielding 2.39 g 4-aminophenylpropionitrile.

(b) The product obtained is coupled with phloroglucinol by dissolving 0.26 g (1.767 mmol) in 10.5 ml diethylether.

10

Zinc chloride (0.45 g; 3.286 mmol) and 0.23 g (1.767 mmol) phloroglucinol are added, and a dry HCl gasflow is then lead through the solution for 1.5 hour.

After evaporation of the solvent, the residue is dissolved in 5 ml water and refluxed for 2 hours. After cooling to room temp., the precipitate is sucked off. The desired coupling product (13) is obtained in a yield of 0.319 g (64%)

(c) The product (13) is radiohalogenated in two steps, in a corresponding manner as described in Example I, yielding in the first step the Br-substituted product (14; $X_1$=Br) and thereupon the desired $^{123}$I-substituted product: (14; $X_1=^{123}$I).

EXAMPLE IV

Preparation of radiohalogenated 4-carboxy-phloretin analogue

(a) The Br-substituted 4-amino-phloretin analogue (14; $X_1$=Br) is used as a starting compound in this synthesis. 0.88 g (2.5 mmol) of this compound is dissolved in 1.1 ml tetrafluoroboric acid. To this solution, while cooling in an ice bath and vigorously stirring, a cooled solution of 0.17 g sodium nitrite (2.5 mmol) in 0.34 ml water is added dropwise. Then the diazonium salt formed is filtered and washed succesively with cooled tetrafluoroboric acid, ethanol and diethylether (many times). The diazonium salt (15) is obtained in a yield of 1.08 g (96%)

(b) The product obtained (15) (1.12 g; 2.5 mmol) is, together with 0.62 g sodium acetate (7.5 mmol), 0.0113 g palladium acetate (0.05 mmol) and 15 ml acetonitrile, cooled in a glass autoclave to 0° C. under a nitrogen atmosphere. After replacing the nitrogen atmosphere by carbon monoxide (9 kg/cm$^2$), the reaction mixture is stirred at room temperature for 1 hour.

After removal of the carbon monoxide, the solvent is evaporated under diminished pressure and the residue is stirred with 5 ml 30% aqueous NaOH solution, after which 10 ml water and 13 ml diethylether are added.

After extraction, the organic phase is washed with NaCl solution. The combined aqueous phases are treated twice with active charcoal and acidified with concentrated hydrochloric acid to pH 1. Extraction (3 times) with diethyl ether and evaporation of diethylether and acetic acid under reduced pressure yields the desired product in a high purity: (16; $X^1$=Br)

(16)

(c) The product is radiohalogenated with $^{123}I$ (as sodium iodide) in a corresponding manner as described in Example I(b), yielding (16; $X_1=^{123}I$).

EXAMPLE V

Preparation of radiohalogenated HOOCCH$_2$NHCO-phloretin analogue (a) 3-(4-Aminophenyl)-1-(2,4,6,-trimethoxyphenyl)-1-propanone is prepared in a corresponding manner as described in Example III(a), using trimethoxybenzene instead of phloroglucinol. The product is converted to the 4-carboxy-substituted compound in a corresponding manner as described in Example IV(a)+(b). This product is brominated in a corresponding manner as described in Example I(a), yielding 3(3-bromo-4-carboxyphenyl)-1-(2,4,6-trimethoxyphenyl)-1propanone.

(b) This product is converted to the N-succinimidyl ester by dissolving 1.27 g (3 mmol) thereof together with 0.35 g N-hydroxysuccinimide (3 mmol) in 4 ml acetonitrile. To this solution is added at 10° C. 0.65 g dicyclohexycarbodiimide (3.2 mmol). The reaction mixture is stirred for 4 hours, allowing the mixture to reach room temperature, after which the mixture is stored at approx. 5° C. for several hours. The mixture is filtered and the filtrate is evaporated in vacuo; the residue is recrystallized yielding 1.35 g (87%) of the desired ester.

(c) The glycine moiety is introduced by treating a solution of 0.23 g glycine (3 mmol) and 0.26 g NaHCO$_3$ (3 mmol) in 3.2 ml water with a solution of 1.04 g (2 mmol) of the above ester in 4 ml 1,2-dimethoxyethane. After 1 hour, 2 ml water is added and the solution is acidified with concentrated HCl solution to pH 2. After cooling in an ice-water bath for 0.5 hour, the precipitate is sucked off, giving the desired-product (17) in a yield of 0.72 g (75%)

(17)

(d) In a corresponding manner as described in Example II(d) product (17) is deprotected, viz. by dissolving 1.73 g (3.6 mmol) in 5 mnl dichloromethane and treating this reaction mixture under an inert atmosphere and while cooling in dry ice/isopropanol with borotrifluoride (1.2 ml, 12 mmol). After stirring for 30 minutes without cooling and then at 0° C. for another 30 minutes, the reaction mixture is saturated with NaCl and extracted with dichloromethane.

The organic phase is dried and concentrated, yielding 1.58 g product (18; $X_1$=Br) (100%).

(18)

(e) the product is radiohalogenated in a corresponding manner as described in Example I(b), producing (18; $X_1=^{123}I$).

EXAMPLE VI

In vitro evaluation of 3-halo-phloretin compounds using the "hexokinase-model".

The "hexokinase-model" is used as a model system for the glucose-transport proteins, which play a paramount role in the glucose metabolism.

The mechanism of the glucose—glucosetransportprotein interaction and following transport through the cell membrane of glucose, as described in literature (Scientific American, January 1992, p. 32–39; Biochemistry, Vol. 28, No. 20, 1989, p. 8221–8227), and the induced-fit model described for glucose 6-phosphorilation by hexokinase (Cell Biology, 1989) show a certain analogy which let to assume, that the interaction between a potential glucose transport inhibitor with hexokinase can be a valuable in vitro model if this inhibition is competitive for glucose.

It was proven from Lineweaver-Burck plots that the inhibition of hexokinase activity by phloretin is competitive and comparable with the type of interaction of deoxyglucose, a substrate that competes with glucose for phosphorilation and can serve as a reference.

The substitution of halogen such as a bromine or iodine atom on the 3-position of the 4-hydroxy-phenylpropion part of phloretin increases the inhibition potency as shown as follows:

Inhibition of hexokinase catalyses 6-phosphorilation of glucose by deoxyglucose, phloretin and 3-bromo-phloretin.

| inhibitor | Ki (inhibition constant*) |
|---|---|
| deoxyglucose | $4.7 \; 10^{-4}M$ |
| phloretin | $0.8 \; 10^{-4}M$ |
| 3-Br-phloretin | $0.8 \; 10^{-4}M$ |
| 3-I-phloretin | $0.4 \; 10^{-4}M$ |

*A smaller Ki value corresponds to a higher inhibition potency.

3-I-phloretin is approx. 2 times a more potent inhibitor for hexokinase than the original phloretin. The above results clearly indicate, that halogenated phloretin is a potentially promising tool in the therapeutic treatment of tumours.

For interaction with transport-proteins the order of magnitude of the Ki values will be lower, but the relative potency will remain.

EXAMPLE VII

In vitro experiments: binding in human whole blood

Jennings et al. |J. Gen. Phys., 1967, 67, 381|have reported the binding of phloretin to whole red blood cells. Their results let to assume that phloretin should enter the erythrocytes and bind to haemoglobine. This should mean that a phloretin-based radiotracer should not be suitable for in vivo use. Therefore the reversibility of the binding is checked. For this purpose 3-$^{125}I$-phloretin is added to whole heparinised blood. This is centrifuged, yielding serum S-*I and red blood portion RB-*I. S-*I and non-radioactive RB (1/1) and respectively non-radioactive S and RB-*I (1/1) are incubated at 37° C. for 15 min and centrifuged. The radioactivity of all the weighed aliquots is measured in a well NaI(Tl) detector.

In whole blood, 3-$^{125}I$-phloretin is bound reversibly to plasma-proteins and RB. Under non-carrier-added (N.C.A.) conditions, the RB/plasma ratio amounts to 0.215, while in the presence of non-radioactive Br-phloretin or phloretin this ratio increases to 0.32 due to low affinity binding. Re-equilibration of radioactivity (N.C.A. added) bound to RB and plasma with the opposite non-radioactive blood component yields 0.15 and 0.13, respectively.

This means, that $3-^{125}$I-phloretin is not irreversibly clustered in the erythrocytes, as could be feared for according to the above publication by Jennings et al., but is suitable for transport by human blood to the tissue of interest.

EXAMPLE VIII

In vitro experiments: binding to erythrocytes as model cells and to cancer cells In order to be able to compare the binding to cancer cells with the binding to normal cells, the following experiments are carried out. Binding to certain cancer cells, viz. YAK1 mice lymphoma cells ($10_6$ cells/ml incubation medium) is compared with binding to erythrocytes of a young healthy man ($10^6$ cells/ml incubation medium), because erythrocytes are typical reference cells for glucose transport studies.

The incubation media are respectively:
RPMI buffer pH=8; 11 mM in glucose, and
RPMI buffer/0.9% NaCl : 1/1.

Each 1 ml essay contains 5% of foetal calf serum and is spiked (50 μl) with $3-^{125}$I-phloretin (initial activity is measured). After 15 min incubation at 37° C., the suspension is centrifuged and the precipitate is resuspended with 1 ml cold buffer which is discarded after a second centrifugation. The final radioactive precipitate is suspended in 1 ml water and measured. The bound radioactivity is related to the initial activity.

Saturation binding of $3-^{125}$I-phloretin to $5.10^6$ erythrocytes is performed in RPMI-buffer and Tris-buffer of pH 8. The binding experiments are performed at pH 8, because this is the pH of the RPMI buffer needed for optimum YAK1 cells growth. Incubation for 15 min at 37° C. Inhibition is studied by pre-incubation (15 min, 37° C.) of the erythrocytes in buffer containing $2.10^{-4}$M 3-Br-phloretin. After centrifugation, the Br-phloretin—containing solution is discarded and the precipitate washed with ice-cooled buffer. After a second centrifugation, the supernatant is discarded and the cells are resuspended in buffer containing $3-^{125}$I-phloretin. After incubation for 15 min at 37° C., the same above procedure is applied.

Phloretin is a weak acid (pK is approx. 7.3); only the uncharged (non-dissociated) form inhibits red cell glucose transport (Jennings et al., see above). Therefore the values mentioned hereinafter are corrected for dissociation.

Figure 1:
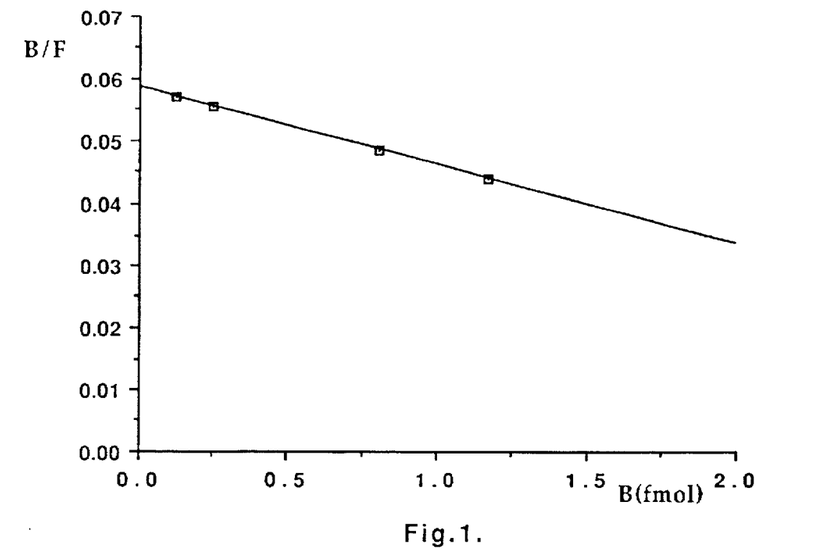
FIG. 1: Rectilinear Scatchard plot of saturation binding from 0.1 to 1.2×10⁻¹⁰M of 3-$^{125}$I-phloretin.
Figure 2:
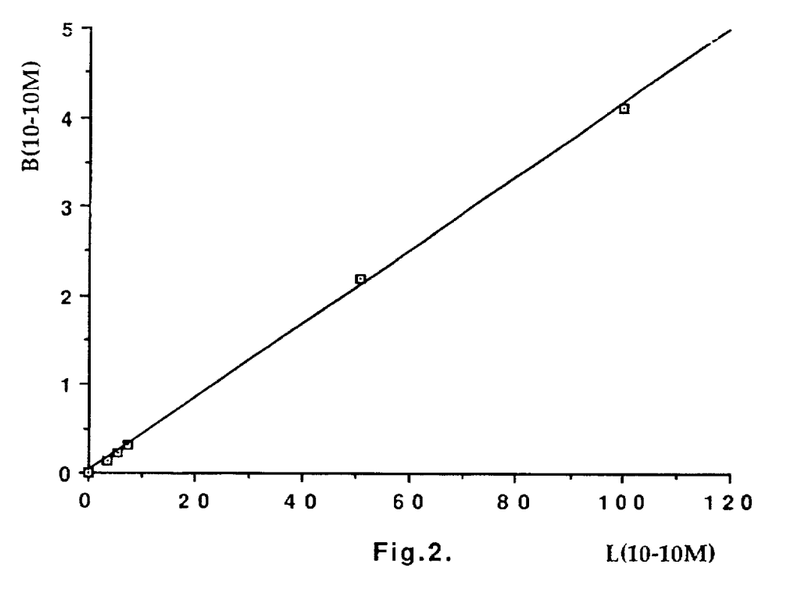
FIG. 2: Binding of C.A. 3-$^{125}$I-phloretin (B in 10⁻¹⁰M) to erythrocytes is plotted against the concentration of 3-$^{125}$I-phloretin (L in 10⁻¹⁰M).

When starting from small amounts ($0.1 \times 10^{-10}$M) N.C.A. $3-^{125}$I-phloretin up to higher concentrations and C.A. conditions (3-Br-phloretin used as analogue), two types of binding are obseved:

(i) Saturation binding from 0.1 to 1.2 $10^{-10}$M $3-^{125}$I-phloretin yields a rectilinear Scatchard plot (FIG. 1), revealing an apparent Kd value of $8 \times 10^{-11}$M and a Bmax of $4.7 \times 10^{-15}$ mol/$10^6$ erythrocytes. In this Figure the B/F ratio is plotted against the binding of 3-I-phloretin to erythrocytes (B in $10^{-15}$ mol). (ii) From $10^{-10}$M up to $1.5 \times 10^{-9}$M a non-specific-like (low-affinity) binding is observed (FIG. 2). In this Figure the binding of C.A. 3-*I-phloretin (B in $10^{-10}$M) to erythrocytes is plotted against the concentration of $3-^{125}$I-phloretin (L in $10^{-10}$M).

Due to the low-affinity binding observed, competitive inhibition can only be studied by pre-incubation (comparable to pre-injection in vivo). Pre-incubation with $2 \times 10^{-4}$M 3-Br-phloretin yields a bound/free value of 0.081 which, compared with 0.193 for the blank, means an inhibition of 58% (each average of 5 experiments).

In case of YAK1 cells a different behaviour is observed. Co-incubation of 3-Br-phloretin does not result in an increased non-specific binding, as for erythrocytes, but in an decreased binding (30%), pointing to inhibition.

It is also observed, that in the presence of serum albumine at equilibrium the high affinity binding remains unchanged while the non-specific-like binding to erythrocytes decreases with an increasing amount of serum proteins. This means, that the strength of the non-specific binding to erythrocytes and serum proteins is approximately comparable and makes blood a suitable and reversible transport medium for $3-^{125}$I-phloretin high affinity binding.

Moreover, the presence of $3.10^{-3}$–$5.10^{-3}$M glucose hardly influences the binding of $3-^{125}$I-phloretin.

Comparison of the binding to cancer cells and to erythrocytes can give valid information about the expected increased glucose transport in tumour cells. The incubation time is limited to 15 min in view of optimum viability of the cell culture used.

Under the experimental conditions the bound/free ratio of N.C.A. $3-^{125}$I-phloretin binding to $10^6$ erythrocytes amounts to 0.021 while for $10^6$ YAK1 cells a value of 0.048 is obtained (average of at least 20 experiments). Under C.A. conditions the inhibition of uptake for erythrocytes depends on the concentration of the carrier (high or low affinity), while for YAK1 cells at higher carrier concentration the amount of bound radioactivity decreases. This indicates, that in case of YAK1 cells only the high affinity binding type is involved. These results show an increased uptake of $3-^{125}$I-phloretin to YAK1 lymphoma cancer cells as compared to erythrocytes; the increase is more than a factor 2. This supports the hypothesis, that higher glucose uptake in tumour cells can be related to an increased amount of transport proteins in the cell membrane. These results clearly show that 3-*I-phloretin, e.g. $3-^{123}$I-phloretin, in potency is a promising SPECT tracer for tumours showing an increased glucose uptake. The $^{125}$I-labelled compound can also be an interesting tool for in vitro characterization of cytological samples of tumour suspected tissues.

EXAMPLE IX

In vivo distribution studies in test animals

The in vivo distribution in rats is determined by injecting approx. 10μCi of the compound to be evaluated into the tail vein of the test animals. The test animals are sacrificed at appropriate time intervals after injection and the radioactivity of the organs of interest is measured by gamma scintillation counting.

Figure 3:
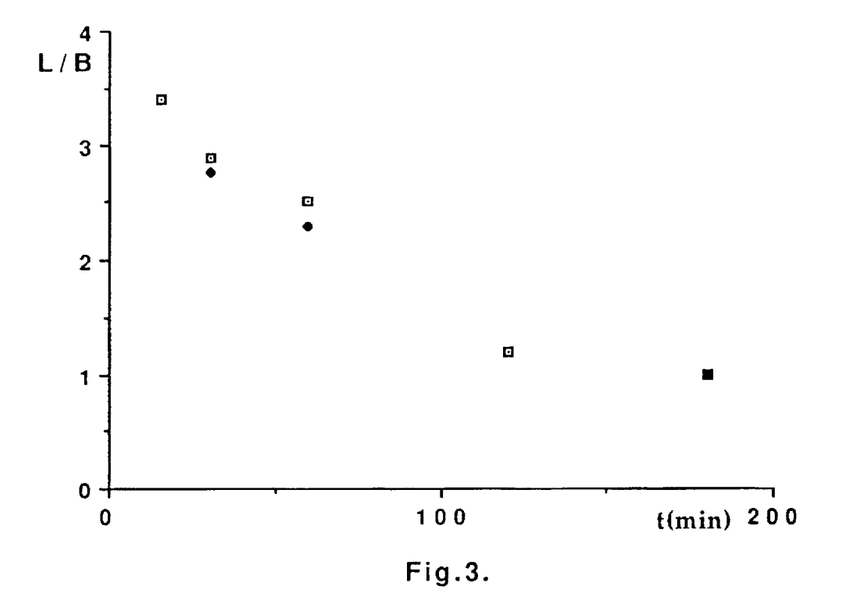
FIG. 3: Uptake of N.C.A. (□) and C.A. (◇) 3-$^{125}$I-phloretin in lung versus blood (L/B) as a function of time.

The observed high uptake in the lungs (FIG. 3) points to a high uptake in the endothelial cells. In FIG. 3 the uptake of N.C.A.(□) and C.A.(◇) 3*I-phloretin in lung versus blood (L/B) is presented as a function of the time.

Figure 4:
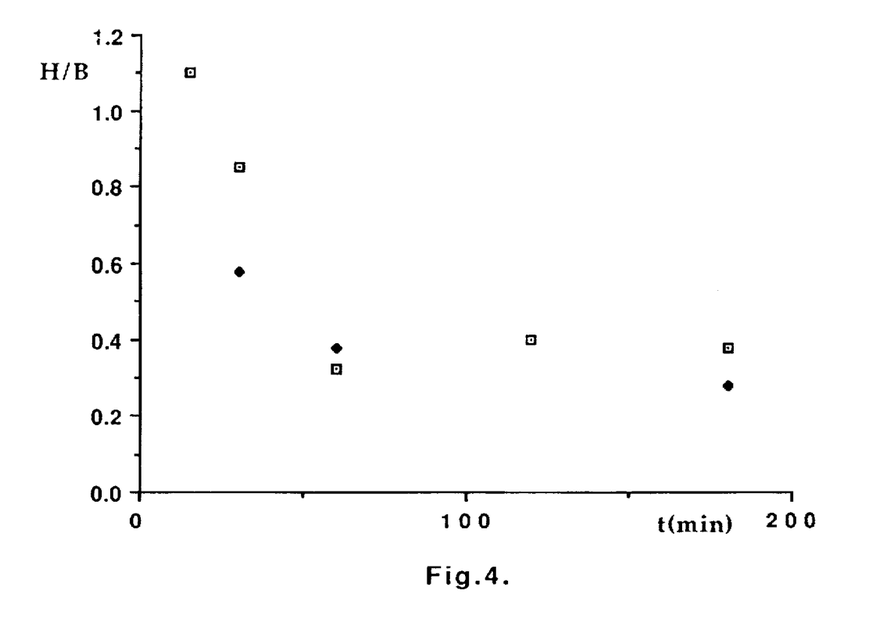
FIG. 4: Uptake of N.C.A. (□) and C.A. (◇) 3-$^{125}$I-phloretin in heart versus blood (H/B) as a function of time.
Figure 5:
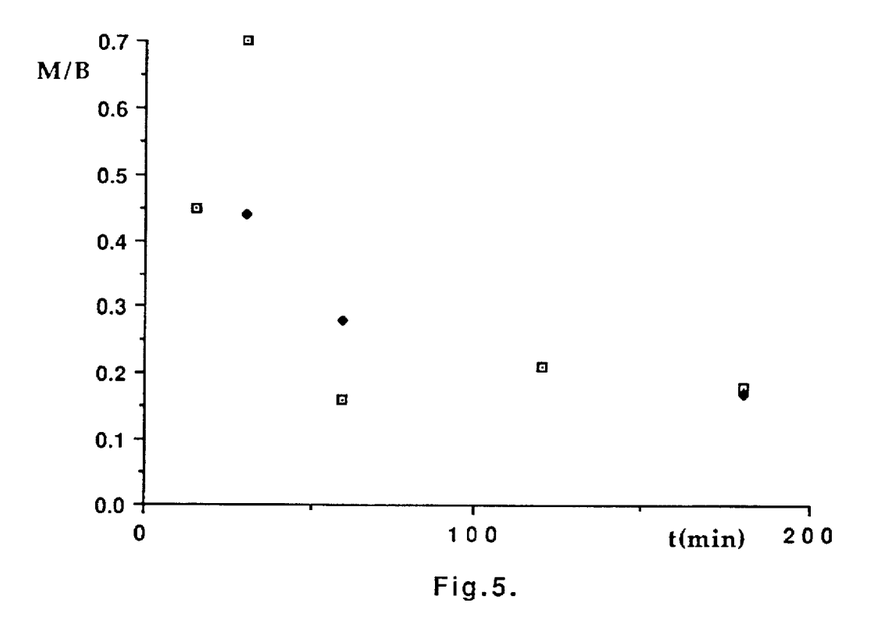
FIG. 5: Uptake of N.C.A. (□) and C.A. (◇) 3-$^{125}$I-phloretin in muscle versus blood (M/B) as a function of time.

Glucose uptake in myocardial cells and in myoblasts are known to be rate limited. FIGS. 4 and 5 present the uptake of N.C.A.(□) and C.A.(◇) 3-*I-phloretin in heart and muscle, respectively, in relation to the uptake in blood ((H/B and M/B, respectively), as a function of the time. As shown in FIG. 4 and FIG. 5, the uptake in the heart and muscle, reaching a maximum value around respectively 15 min and 30 min post-injection, is apparently saturable, as appears from the decreased uptake in the presence of Br-phloretin. This points to a high affinity site uptake. From the results

15 obtained, the conclusion can be drawn, that 3*I-phloretin, in particular 3-$^{123}$I-phloretin, is potentially a promising tracer to study early myocardial uptake and pathologies related to muscle.

I claim:

1. A method of detecting and locating tissues, having a disturbed glucose metabolism or an increased tyrosine kinase activity, in the body of a warm-blooded living being, which comprises (i)administering to said being a composition comprising, in an effective amount for external imaging, a pharmaceutical composition, comprising (a) a pharmaceutically acceptable carrier material; and (b) a polyhydric phenol compound of the general formula (I)

wherein

R is a hydrogen atom or a saccharide moiety;

A and B are hydrogen atoms or form together a C—C bond;

$R_1$ is a hydroxy group and $R_2$ is a hydrogen atom, or

$R_1$ is and $R_2$ form together an oxygen atom;

Z is a hydroxy group, an amino group, a carboxy group or a N-(carboxymethyl)carbamoyl group;

X* is $^{123}$I, $^{131}$I, $^{75}$Br, $^{76}$Br or $^{77}$Br; and m and n are 0 or 1, with the proviso, that m is 1 if n is 0, and that m is 0 if n is 1; and thereupon (ii) subjecting said being to external imaging to determine the targeted sites in the body of said being in relationship to the background activity.

2. The method of claim 1 in which the phenol compound has the general formula

(II)

wherein

R, $R_1$, $R_2$, Z, A and B have the meanings given in claim 1; and

Y* is a radioactive halogen isotope selected from $^{123}$I, $^{124}$I, $^{125}$I, $^{131}$I, $^{75}$Br, $^{76}$Br, $^{77}$Br or $^{82}$Br.

3. The method of claim 1 in which the phenol compound has the general formula (III)

wherein

Y* has the same meaning as X*.

4. A method of intraoperatively detecting and locating tissues, having a disturbed glucose metabolism or an increased tyrosine kinase activity, in the body of a warm-blooded living being, which comprises (1) administering to said being a composition comprising, in an effective amount

16 for detection by a gamma detecting probe, a radiolabeled polyhydric phenol compound of the general formula (I)

wherein

R is a hydrogen atom or a saccharide moiety;

A and B are hydrogen atoms or form together a C—C bond;

$R_1$ is a hydroxy group and $R_2$ is a hydrogen atom, or

$R_1$ is and $R_2$ form together an oxygen atom;

Z is a hydroxy group, an amino group, a carboxy group or a N-(carboxymethyl)carbamoyl group;

X* is $^{123}$I, $^{125}$I, or $^{125}$I; and m and n are 0 or 1, with the proviso, that m is 1 if n is 0, and that m is 0 if n is 1; and thereupon (ii), after allowing the active substance to be taken up in said tissues and after blood clearance of radioactivity, subjecting said being to a radioimmunodetection technique of the targeting site of the body of said being, by using a gamma detecting probe.

5. The method of claim 4 wherein the phenol compound has the general formula

(II)

wherein

R, $R_1$, $R_2$, Z, A and B have the meanings given in claim 1; and

Y* is a radioactive halogen isotope selected from $^{123}$I, $^{124}$I, $^{125}$I, $^{131}$I, $^{75}$Br, $^{76}$Br, $^{77}$Br or $^{82}$Br.

6. The method of claim 4 wherein the phenol compound has the general formula (III)

wherein

Y* has the same meaning as X*.

7. A method of therapeutically treating tumors, having an increased glucose uptake or an increased tyrosine kinase activity, in the body of a warm-blooded living being, which comprises administering to said being a composition comprising, in an effective amount for combating or controlling tumors, a radiolabeled polyhydric phenol compound of the general formula (I)

wherein

R is a hydrogen atom or a saccharide moiety;

A and B are hydrogen atoms or form together a C—C bond;

$R_1$ is a hydroxy group and $R_2$ is a hydrogen atom, or

$R_1$ is and $R_2$ form together an oxygen atom;

Z is a hydroxy group, an amino group, a carboxy group or a N-(carboxymethyl)carbamoyl group;

X* is $^{124}$I, $^{125}$I, or $^{131}$I; and m and n are 0 or 1, with the proviso, that m is 1 if n is 0, and that m is 0 if n is 1.

8. The method of claim 7 wherein the phenol compound has the general formula

(II)

wherein

R, $R_1$, $R_2$, Z, A and B have the meanings given in claim 1; and

Y* is a radioactive halogen isotope selected from $^{123}$I, $^{124}$I, $^{125}$I, $^{131}$I, $^{75}$Br, $^{76}$Br, $^{77}$Br or $^{82}$Br.

9. The method of claim 7 wherein the phenol compound has the general formula (III)

wherein Y* has the same meaning as X*.

* * * * *